United States Patent [19]

Marsili et al.

[11] 4,305,941
[45] Dec. 15, 1981

[54] RIFAMYCIN XII DERIVATIVES, THEIR PREPARATION AND ANTI-BACTERIAL COMPOSITIONS THEREOF

[75] Inventors: Leonardo Marsili, Segrate; Giovanni Franceschi; Aurora Sanfilippo, both of Milan, all of Italy

[73] Assignee: Farmitalia Carlo Erba S.p.A., Milan, Italy

[21] Appl. No.: 222,618

[22] Filed: Jan. 5, 1981

[30] Foreign Application Priority Data

Feb. 13, 1980 [GB] United Kingdom .............. 04848/80

[51] Int. Cl.³ .................. A61K 31/415; C07D 521/00
[52] U.S. Cl. ....................... 424/248.54; 260/239.3P; 424/250; 424/267; 424/258; 424/273 B
[58] Field of Search ............. 260/239.3 P; 424/273 B, 424/248.54, 258, 267; 421/250

[56] References Cited

U.S. PATENT DOCUMENTS

| | | | |
|---|---|---|---|
| 4,086,225 | 4/1978 | Marsili et al. | 260/239.3 P |
| 4,164,499 | 8/1979 | Rossetti et al. | 260/239.3 P |
| 4,165,317 | 8/1979 | Rossetti et al. | 260/239.3 P |
| 4,219,478 | 8/1980 | Marsili et al. | 260/239.3 P |
| 4,226,765 | 10/1980 | Marsili et al. | 260/239.3 P |

*Primary Examiner*—Robert T. Bond
*Attorney, Agent, or Firm*—Oblon, Fisher, Spivak, McClelland & Maier

[57] ABSTRACT

Novel rifamycin derivatives having the formula:

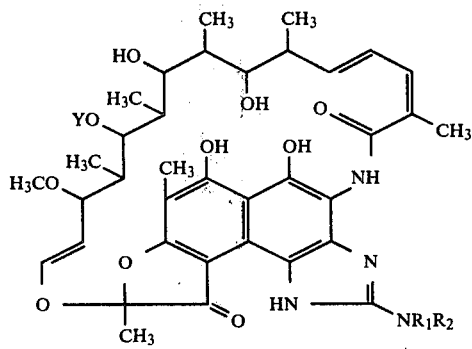

wherein Y is —H or —COCH$_3$; R$_1$ and R$_2$ may be linear or branched alkyl having from 1 to 7 carbon atoms and alkenyl having 3 or 4 carbon atoms R$_2$ may be also chloroalkyl having from 2 to 4 carbon atoms, cycloalkyl having from 3 to 7 carbon atoms in the ring, cycloalkylalkyl having from 3 to 6 carbon atoms in the ring, phenyl, bornyl, arylalkyl hydrocarbon having 7 or 8 carbon atoms which may be substituted with one halogen atom in the aryl group; and R$_1$ and R$_2$ along with the N atom to which they are bonded form an unsubstituted cyclic moiety having from 5 to 8 carbon atoms, a cyclic moiety having from 5 to 8 carbon atoms substituted with 1 or 2 methyl radicals, 4-alkylpiperazine, morpholine, 1,2,3,4-tetrahydroisoquinoline. These novel compounds are yellow-orange solids having high antibacterical activity which are obtained by reacting 3-amino-4-deoxo-4-imino rifamycin S with a chloroformiminium chloride.

8 Claims, No Drawings

RIFAMYCIN XII DERIVATIVES, THEIR PREPARATION AND ANTI-BACTERIAL COMPOSITIONS THEREOF

The invention relates to S and SV rifamycin derivatives, to methods for their preparation and to pharmaceutical composition containing them.

The invention provides rifamycin compounds having the general formula I

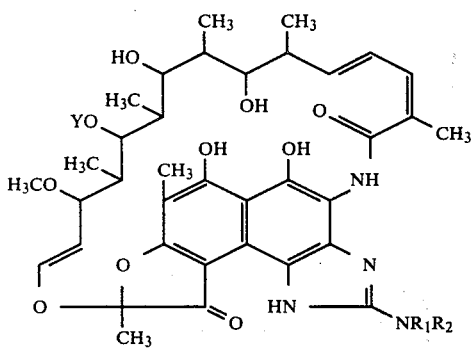

wherein Y represents a hydrogen atom or an acetyl group, and either $R_1$ represents a linear or branched alkyl group having from 1 to 7 carbon atoms or an alkenyl group having 3 or 4 carbon atoms, and $R_2$ represents a linear or branched alkyl group having from 1 to 7 carbon atoms, a chloroalkyl group having from 2 to 4 carbon atoms, an alkenyl group having 3 or 4 carbon atoms, a cycloalkyl group having from 3 to 7 carbon atoms in the ring, a cycloalkylalkyl group having 3 to 6 carbon atoms in the ring, a phenyl or bornyl group, an unsubstituted aralkyl group having 7 or 8 carbon atoms, or an aralkyl group having 7 or 8 carbon atoms and substituted by one halogen atom in the aryl group, or $R_1$ and $R_2$ together with the nitrogen atom to which they are bonded represent an unsubstituted cyclic moiety having from 5 to 8 carbon atoms, a cyclic moiety having from 5 to 8 carbon atoms substituted by one or two methyl group(s), a 4-alkyl-1-piperazinyl group or a morpholino or 1,2,3,4-tetrahydroisoquinolinyl group.

The invention also provides compounds of the general formula II

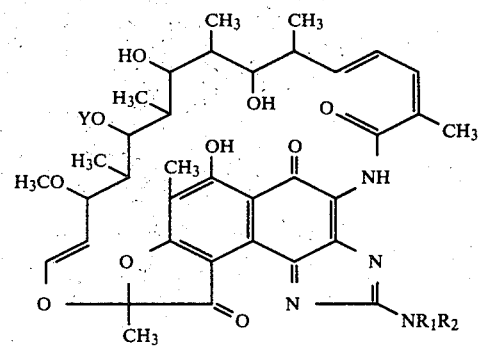

wherein Y, $R_1$ and $R_2$ are as above defined. These compounds of the general formula II are oxidation products of the compounds of the general formula I.

The rifamycin compounds according to the invention have antibacterial activity against Gram-positive and Gram-negative bacteria and against Mycobacterium Tuberculosis. The compounds of the general formula I are yellow-orange solids, while those of the general formula II are green solids. They are generally soluble in most organic solvents, such as chlorinated solvents, alcohols and esters and are partially soluble in aromatic hydrocarbons. The compounds of the general formula I are generally soluble in aqueous solutions at a pH of between 7 and 8, whereas the compounds of the general formula II are substantially insoluble in water.

The compounds of the general formula I may be prepared by a process comprising reacting 3-amino-4-deoxo-4-imino-rifamycin S of the general formula III

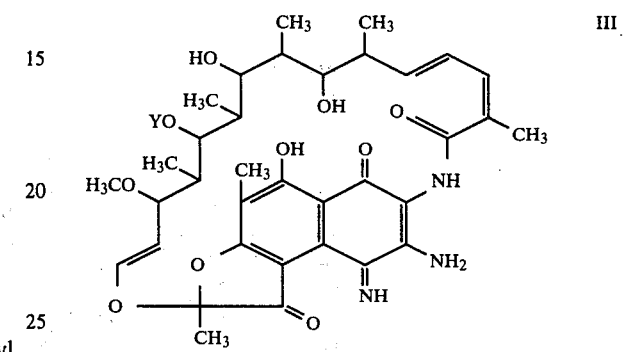

wherein Y represents a hydrogen atom or an acetyl group, in the presence of a tertiary amine and of an aprotic solvent, with a chloroformiminium chloride of the general formula IV

wherein $R_1$ and $R_2$ are as above defined. This process is within the scope of the invention.

The compounds of the general formula III are disclosed in British Patent Specification No. 1,534,075. The compounds of the general formula IV are described in British Patent Specification No. 1,293,590. The rifamycin compounds according to the invention may be admixed with a pharmaceutically acceptable carrier or diluent to form a pharmaceutical composition within the scope of the invention. Whether alone or in such a composition, they may be formulated for administration in conventional unit dosage forms.

It should be noted that in the Examples the C atoms in the PMR spectra are numbered according to IUPAC rules.

The invention is illustrated by the following Examples.

EXAMPLE 1

3-amino-4-deoxy-4-amino-3,4-imidazolyl-(3'H)-[2'(N-piperidyl)]rifamycin SV 8 g of 3-amino-4-deoxo-4-imino-rifamycin S were dissolved in 100 ml of dichloromethane, 7 ml of triethylamine were added and the solution was cooled to −40° C.

A solution of 8 g of chloropiperidylformiminium chloride in 50 ml of dichloromethane was added dropwise and the temperature was kept at −40° C. for 60 minutes. The solution was gently warmed to room temperature, washed with diluted acetic acid and then with water. After drying on anhydrous sodium sulphate the solution was concentrated to 30 ml. 10 ml of petroleum ether were added and the solution was allowed to crystallize. 0.6 g of an orange compound of the general formula I, wherein Y=COCH$_3$ and NR$_1$R$_2$=piperidyl, were obtained.

PMR (CDCl$_3$): −0.35 δ [d, CH$_3$—C(22)]; 0.43 δ [d,CH$_3$—C(20)]; 0.88 δ [d,CH$_3$—C(16)]; 1.04 δ [d,CH$_3$—C(18)]; 1.82 δ [s,CH$_3$—C(2)]; 2.00 δ ]s,CH$_3$—COO—C(21)]; 2.11 δ ]s, CH$_3$—C(12)]; 2.19 δ [s,CH$_3$—C(4)]; 3.04 δ [s, CH$_3$—O];

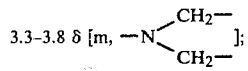

3.3-3.8 δ [m, 4.6-5.4 δ [m, C(21)H and C (24)H]; 6.0-6.6 [m, C(13)H, C(14)H, C(15)H and C(25)H]; 8.90 δ [s, N(3')H]; 13.07 δ [s, C(5)OH and C(6)OH].

MS: 804 (M+)

EXAMPLE 2

3-amino-4-deoxy-4-amino-3,4-imidazolyl-(3'H)-2'-morpholinorifamycin SV 8 g of 3-amino-4-deoxo-4-imino-rifamycin S were dissolved in 100 ml of tetrahydrofuran. 10 ml triethylamine were added, the temperature was lowered to 0° C. and 8 g of chloromopholinoformiminium chloride were added portionwise.

After stirring for 60 minutes at 0° C. and 120 minutes at ambient temperature the solution was added dropwise to 600 ml of water containing 15 ml of acetic acid. The precipitate obtained was filtered off, washed with water and then dissolved in 500 ml of diethyl ether. The organic solution was extracted with a phosphate buffer solution at pH 7.5. The aqueous phase was then acidified to pH 6 with acetic acid and extracted with dichloro methane. After washing with water and drying on anhydrous sodium sulphate, the dichloromethane solution was concentrated to 10 ml and 30 ml of petroleum ether were then added. 0.45 g of a crude product was obtained and then purified by column chromatography on silica gel eluting with 96:4 chloroform:methanol.

Yield 0.400 g of a compound of the general formula I wherein Y=COCH$_3$ and NR$_1$R$_2$=morpholino.

PMR (CDCl$_3$): −0.49 δ [d, CH$_3$—C(22)]; 0.38 δ [d,CH$_3$—C(20)]; 0.87 δ [d, CH$_3$—C(16)]; 1.01 δ ]d,CH$_3$—C(18)]; 1.80 δ [s,CH$_3$—C(2)]; 2.00 δ [s, CH$_3$—COO—C(21)]; 2.10 δ [s, CH$_3$—C(12)]; 2.22 δ [s,CH$_3$—C(4)]; 3.03 δ [s, CH$_3$—O];

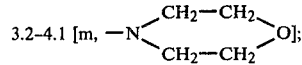

3.2-4.1 [m, 4.6-5.4 δ [m, C(21)H and C(24)H]; 6.0-6.6 δ [m, C(13)H, C(14)H, C(15)H and C(25)H]; 8.57 δ [bs,N(3')H]; 12.27 and 13.60 δ [bs, C(5)OH and C(6)OH].

MS: 806 (M+)

EXAMPLE 3

3-amino-4-deoxy-4-amino-3,4-imidazolyl-(3'H)-[2'(hexahydro-1H-azepin-1-yl)]rifamycin SV 8 g of 3-amino-4-deoxo-4-imino-rifamycin S were dissolved in 100 ml tetrahydrofuran, 8.5 ml of triethylamine were added and the temperature was lowered to 0° C. 7 g of chlorohexahydroazepinylformiminium chloride were added portionwise and the solution was stirred for 120 minutes at room temperature. 300 ml of dichloromethane were added, the organic solution was washed with diluted acetic acid and then with water, and finally was dried on anhydrous sodium sulphate. The solvent was evaporated off and the crude product was purified by column chromatography on silica gel, eluting with 99:1 chloroform:methanol.

Yield: 0.75 g of a compound of the general formula I wherein Y=COCH$_3$ and NR$_1$R$_2$=hexahydroazepinyl.

PMR (CDCl$_3$): −0.24 δ [d, CH$_3$—C(22)]; 0.43 δ [d, CH$_3$—C(20)]; 0.85 δ [d,CH$_3$—C(16)]; 1.03 δ [d, CH$_3$—C(18)]; 1.83 δ [s,CH$_3$—C(2)]; 1.99 δ [s, CH$_3$—COO—C(21)]; 2.13 δ [s, CH$_3$—C(12)]; 2.20 δ [s,CH$_3$—C(4)]; 3.06 δ [s, CH$_3$—O];

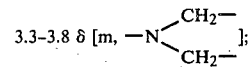

3.3-3.8 δ [m, 4.82 δ [bd, C(21)H]; 5.35 δ [dd,C(24)H]; 6.0-6.5 δ [m,C(13)H,C(14)H, C(15)H,C(25)H]; 8.43 δ [s, N(3')H]; 11.70 and 12.97 δ [bs, C(5)OH and C(6)OH].

MS: 818 (M+).

EXAMPLE 4

3-amino-4-deoxy-4-amino-3,4-imidazolyl-(3'H)-2'-N-dimethylaminorifamycin SV 8 g of 3-amino-4-deoxo-4-amino-rifamycin S were dissolved in 40 ml of dichloromethane, 8 ml of triethylamine were added and the temperature was lowered to 0° C. 5.5 g chlorodimethylformiminium chloride were added portionwise and the solution was stirred for 30 minutes at ambient temperature. 100 ml of dichloromethane were added, the organic solution was washed with diluted acetic acid and then with water, and finally was dried over anhydrous sodium sulphate. After filtration, 100 ml of petroleum ether were added, the precipitate was filtered off and the solvent was evaporated. The crude product thus obtained was purified by column chromatography on silica gel eluting with chloroform:methanol 95:5. Yield: 1.0 g of a compound of the general formula I wherein Y=COCH$_3$ and R$_1$=R$_2$=CH$_3$.

PMR (CDCl$_3$): −0.35 δ [d,CH$_3$—C(22)]; 0.39 δ [d, CH$_3$—C(20)]; 0.86 δ [d,CH$_3$—C(16)]; 1.03 δ [d,CH$_3$—C(18)]; 1.80 δ [s, CH$_3$—C(2)]; 1.97 δ [s, CH$_3$—COO—C(21)]; 2.08 δ [s,CH$_3$—C(12)]; 2.19 δ [s,CH$_3$—C(4)]; 3.04 δ [s, CH$_3$—O]; 3.21 δ [s,N(CH$_3$)$_2$]; 4.6-5.5 δ [m, C(21)H and C(24)H]; 6.0-6.7 δ [m,C(13)H, C(14)H,C(15)H,C(25)H]; 8.53 δ [bs, N(3')H]; 12.00 and 12.23 δ [bs, C(5)OH and C(6)OH].

MS: 764 (M+).

EXAMPLE 5

3-amino-4-deoxy-4-amino-3,4-imidazolyl-(3'H)-[2'-(N-pirrolidinyl)]rifamycin SV 8 g of 3-amino-4-deoxo-4-imino-rifamycin S were dissolved in 40 ml of tetrahydrofuran. 10 ml triethylamine and 7, 5 g of chloropirrolidinylformiminium chloride were added portionwise, the temperature was allowed to rise up to 40° C. and the solution was stirred for 30 minutes. 100 ml of chloroform were added, the solution was washed with diluted acetic acid and then with water: the organic phase was dried on anhydrous sodium sulphate and then concentrated to 30 ml.

10 ml petroleum ether were added, the solution was allowed to crystallize for 3 hours at 0° C. 3,5 g of an orange compound of the general formula I, wherein Y=COCH$_3$ and NR$_1$R$_2$=pirrolidyl, were obtained PMR (CDCl$_3$): −0.28 δ [d, CH$_3$—C(22)]; 0.40 δ [d, CH$_3$—C(20)]; 0.85 δ [d,CH$_3$—C(16)]; 1.03 δ [1.03 [CH$_3$—C(18)]; 1.79 δ [s, CH$_3$—C(2)]; 1.95 δ [s,CH$_3$—COO—C(21)]; 2.06 δ [s,CH$_3$—C(12)]; 2.17 δ [s,CH$_3$—C(4)]; 3.03 δ [s,CH$_3$O—C(23)]; 3.56 δ [m, 2 CH$_2$—N]; 4.7–5.5 δ [m, C(21)H and C(24)H]; 5.9–6.6 δ [m, C(13)H, C(14)H,C(15)H and C(25)H];

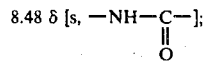

12.0 and 13.29 δ [s, C(5) OH and C(6)OH].

MS: 790 (M+)

EXAMPLE 6

3-amino-4-deoxy-4-amino-3,4-imidazolyl-(3'H)-[2'-N-(4-metil-piperazinyl)]rifamycin SV 8 g of 3-amino-4-deoxo-4-imino-rifamycin S were dissolved in 40 ml of tetrahydrofuran. 10 ml triethylamine and then 9,5 g of 4-methyl-chloropi-perazinylformiminium chloride were added portionwise at +5° C. After 30 minutes the reaction mixture was diluted with 200 ml chloroform, the solution was washed with diluted acetic acid and then with water: the organic phase was dried on anhydrous sodium sulphate and then evaporated to dryness. The crude residue was dissolved in 300 ml of ethyl acetate and the solution was washed with a 2% sodium bicarbonate aqueous solution. The aqueous phase was washed with ethyl ether, acidified with acetic acid to pH 3,5 and then extracted with chloroform. The organic phase was washed with water, dried on anhydrous sodium sulphate and evaporated to dryness. The residue was crystallized from acetone-petroleum ether. 2,2 g of a red compound of the general formula I, wherein Y=COCH$_3$ and NR$_1$R$_2$=4-methyl-piperazinyl, were obtained.

PMR (CDCl$_3$): from −0.5 δ to −0.25 δ [bd, CH$_3$—C(22)]; 0.41 δ [d, CH$_3$—C(20)]; 0.86 δ [d, CH$_3$—C(16)]; 1.02 δ [d, CH$_3$—C(18)]; 1.78 δ [5, CH$_3$—C(2)]; 2.00 δ [s,CH$_3$—COO—C(21)];2.08 δ [s, CH$_3$—C(12)]; 2.21 δ [s, CH$_3$—C(4)]; 2.38 δ [s, CH$_3$—N<]; 2.56 δ [s,2 CH$_2$αN—CH$_3$]; 3.03 δ [s, CH$_3$O—C(23)]; 3.61 δ [bs, 2 CH$_2$βN-CH$_3$]; 4.7–5.5 δ [m, C(21)H and C(24)H]; 6.1–6.6 δ [m, C(13)H, C(14)H, C(15)H and C(25)H];

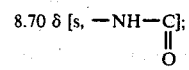

11.71 and 12.50 δ [bs, C(5)OH and C(6)OH].

MS: 819 (M+).

EXAMPLE 7

3-amino-4-deoxy-4-amino-3,4-imidazolyl-(3'H)-2'-N-diisopropylamino-rifamycin SV 8 g of 3-amino-4-deoxo-4-imino-rifamycin S were dissolved in 40 ml of tetrahydrofuran 10 ml triethylamine and then 7 g of chlorodiisopropylformiminium chloride were added portionwise at 0° C. After 20 minutes stirring the reaction mixture was diluted with 100 ml dichloromethane, washed with diluted acetic acid and then with water: the organic phase was dried on anhydrous sodium sulphate and then concentrated to 50 ml. 30 ml of petroleum ether were added and the solution was allowed to crystallize at +5° C. 2,7 g of a red compound of the general formula I, wherein Y=COCH$_3$ and

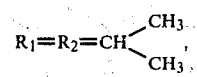

were obtained.

PMR (CDCl$_3$): −0.28 δ [d, CH$_3$—C(22)]; 0.47 δ [d, CH$_3$—C(20)]; 0.81 δ [d,CH$_3$—C(16)]; 1.02 δ [d,CH$_3$—C(18)];

$$1.52\ \delta[d, \begin{matrix}(CH_3)_2-CH\\ (CH_3)_2-CH\end{matrix}N-;$$

1.78 δ [s, CH$_3$—C(2)]; 1.97 δ [s, CH$_3$—COO—C(21)]; 2.12 δ [s, CH$_3$—C(12)]; 2.15 δ [s, CH$_3$—C(4)]; 3.05 δ [s, CH$_3$—O—C(23)]; 4.7–5.4 δ [m, C(21)H and C(24)H]; 6.0–6.4 δ [m,C(13)H,C(14)H,C(15)H and C(25)H];

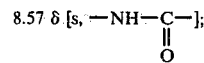

12.17 and 13.57 δ [s, C(5)OH and C(6)OH].

MS: 820 (M+).

The activity in vitro of the rifamycin compounds obtained as described in Examples 1 and 2 have been tested against some Gram-positive and Gram-negative microorganisms and against *Mycobacterium Tuberculosis* (serial dilution method). The results are set out in the following Table, wherein the figures are the values of the minimal inhibiting concentration (MIC) given in mcg/ml.

TABLE

| Microorganisms | Example 1 | Example 2 |
|---|---|---|
| *Staphylococcus aureus* 209 P | 0.0025 | 0.0045 |
| *Streptococcus faecalis* | 0.15 | 0.3 |
| *Staphylococcus aureus* 209 P (Rifampicin resistant) | >200 | >200 |
| *Escherichia coli* B | 10 | 10 |
| *Klebsiella pneumoniae* | 10 | 20 |
| *Escherichia coli* Gin. | 5 | 10 |
| *Escherichia coli* C$_1$ (Rifampicin resistant) | 200 | >200 |
| *Pseudomonas aeruginosa* | 5 | 10 |
| *Salmonella abortivoequina* | 2.5 | 10 |
| *Mycobacterium tuberculosis* H$_{37}$Rv | 0.005 | 0.005 |

What we claim is:

1. A rifamycin having the formula

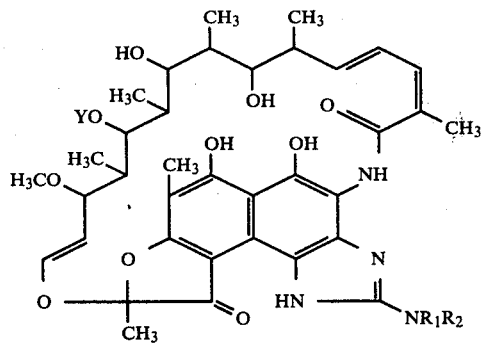

wherein: Y is —H or —COCH$_3$; R$_1$ is selected from the group consisting of linear or branched alkyl having from 1 to 7 carbon atoms, and alkenyl having 3 or 4 carbon atoms; R$_2$ is selected from the group consisting of linear or branched alkyl having from 1 to 7 carbon atoms, chloroalkyl having from 2 to 4 carbon atoms, alkenyl having 3 or 4 carbon atoms, cycloalkyl having from 3 to 7 carbon atoms in the ring, cycloalkylalkyl having from 3 to 6 carbon atoms in the ring, phenyl, bornyl, unsubstituted arylalkyl hydrocarbon having 7 or 8 carbon atoms, arylalkyl hydrocarbon having 7 or 8 carbon atoms and substituted with one halogen atom in the aryl group; and R$_1$ and R$_2$ along with the N atom to which they are bonded form an unsubstituted cyclic moiety having from 5 to 8 carbon atoms, a cyclic moiety having from 5 to 8 carbon atoms substituted with 1 or 2 methyl radicals, 4-alkyl-piperazine, morpholine, 1,2,3,4-tetrahydroisoquinoline.

2. An oxidized compound of formula (I) having the formula

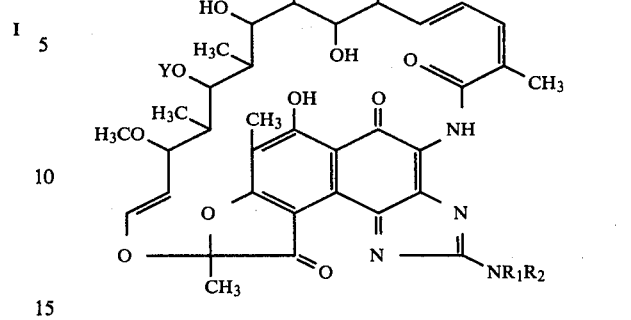

wherein Y, R$_1$ and R$_2$ are as defined in claim 1.

3. Method of preparing a rifamycin of formula (I) according to claim 1, characterized in that a compound of formula

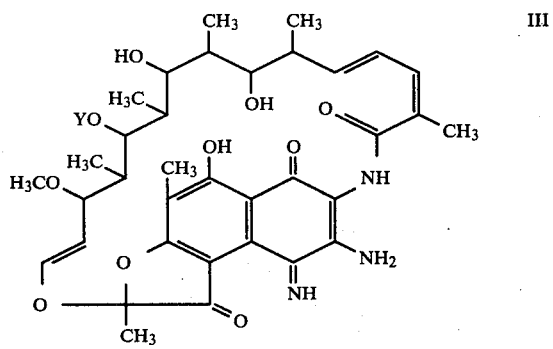

wherein Y is —H or —COCH$_3$ is reacted, in the presence of a tertiary amine and of an aprotic solvent, with a chloroformiminium chloride of formula

wherein R$_1$ and R$_2$ are as defined in claim 1.

4. Method according to claim 3, characterized in that said tertiary amine is triethylamine.

5. Method according to claims 3 and 4, characterized in that said aprotic solvent is selected from the group consisting of tetrahydrofuran and dioxane.

6. Method according to claims 3 and 4, characterized in that said aprotic solvent is selected from the group consisting of methylene chloride, benzene and toluene.

7. A composition which comprises an anti-bacterially effective amount of a rifamycin as claimed in claims 1 or 2, together with a pharmaceutically acceptable carrier or diluent therefor.

8. A composition as claimed in claim 7, in dosage unit form.

* * * * *